US00PP13071P2

(12) United States Plant Patent
Sorensen

(10) Patent No.: US PP13,071 P2
(45) Date of Patent: Oct. 15, 2002

(54) OSTEOSPERMUM PLANT NAMED 'PEMBA'

(75) Inventor: Carl Aksel Kragh Sorensen, Aabyhoj (DK)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/291,105

(22) Filed: Apr. 14, 1999

(51) Int. Cl.[7] ..... A01H 5/00

(52) U.S. Cl. ..... Plt./360

(58) Field of Search ..... Plt./360

(56) References Cited

PUBLICATIONS

UPOV CD–ROM, PBR 961163, Osteospermum designated Pemba, 1996.*
UPOV CD–ROM, PBR 10847, Osteospermum designated Pemba, 1998.*

* cited by examiner

*Primary Examiner*—Bruce R. Campell
*Assistant Examiner*—June Hwu
(74) *Attorney, Agent, or Firm*—C. A. Whealy

(57) ABSTRACT

A distinct cultivar of Osteospermum plant named 'Pemba', characterized by its upright plant habit; numerous inflorescences per plant; and spoon-shaped dark pink ray florets with blue disc florets.

1 Drawing Sheet

BACKGROUND OF THE INVENTION

The present invention relates to a new and distinct cultivar of Osteospermum plant, botanically known as *Osteospermum ecklonis* and referred to by the cultivar name Pemba.

The new cultivar is a product of a planned breeding program conducted by the Inventor in Aabyhoj, Denmark. The objective of the breeding program was to create new Osteospermum cultivars with interesting ray floret colors.

The new cultivar originated from a cross made by the Inventor in 1995 of a proprietary selection of *Osteospermum ecklonis* identified as 9511 as the female, or seed, parent and a proprietary selection of *Osteospermum ecklonis* identified as 9524 as the male, or pollen, parent. The new Osteospermum was selected by the Inventor as a flowering plant within the progeny of this cross in a controlled environment in Aabyhoj, Denmark, in 1996.

Plants of the new cultivar are different from plants of the female parent, the selection 9511, in ray floret color.

Plants of the new Osteospermum are different from plants of the male parent, the selection 9524, in plant size and coloration of lower surface of ray florets.

Asexual propagation of the new cultivar by terminal cuttings at Aabyhoj, has shown that the unique features of this new Osteospermum are stable and reproduced true to type in successive generations.

SUMMARY OF THE INVENTION

The following traits have been repeatedly observed and are determined to be the unique characteristics of 'Pemba'. These characteristics in combination distinguish 'Pemba' as a new and distinct cultivar:

1. Upright plant habit.

2. Numerous inflorescences per plant.

3. Spoon-shaped dark pink ray florets with blue disc florets.

The new cultivar can be compared to the Osteospermum cultivar Sunny Sonja, disclosed in U.S. Plant Pat. No. 10,341. In side-by-side comparisons conducted in Encinitas, Calif., plants of the new cultivar are taller; more freely branching; have more numerous but smaller leaves; are more floriferous; and have longer peduncles than plants of the cultivar Sunny Sonja.

The cultivar Pemba has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical flowering plant of 'Pemba'.

The photograph at the bottom of the sheet is a close-up view of typical inflorescences and young and mature leaves of 'Pemba' (code number 9607 in the photograph) and 'Sunny Sonja' (Sonja in the photograph). Foliage and floret colors in the photographs may appear different from the actual colors due to light reflectance.

DETAILED BOTANICAL DESCRIPTION

The following observations, measurements and values describe one-gallon containers of the new cultivar grown in Encinitas, Calif., under outdoor, full-sun conditions with day temperatures ranging from 20 to 27° C. and night temperatures ranging from 6 to 14° C. Plants were pinched (terminal apex removed) one time about two weeks after planting rooted cuttings. Plants used for this description were grown for about 12 to 14 weeks after planting rooted cuttings.

Color references are made to The Royal Horticultural Society Colour Chart except where general terms of ordinary dictionary significance are used.

Botanical classification: *Osteospermum ecklonis* cultivar Pemba.

Parentage:

*Female, or seed, parent*.—Proprietary selection of *Osteospermum ecklonis* identified as 9511.

*Male, or pollen, parent*.—Proprietary selection of *Osteospermum ecklonis* identified as 9524.

Propagation:

*Type*.—By terminal cuttings.

*Time to initiate roots*.—About 10 days at 18° C.

*Time to develop roots*.—About 21 days at 18° C.

*Rooting habit*.—Fibrous.

Plant description:

*Appearance*.—Perennial herbaceous container and garden plant. Broad inverted triangle. Upright with mounded canopy. Freely branching with about ten primary and about 18 secondary branches. Full plants with dense foliage and erect flower stems.

*Vigor*.—Vigorous.

*Plant height*.—About 31 cm.

*Plant spread*.—About 52 cm.

*Lateral branch description*.—Length: About 12 to 16 cm. Diameter: Primary, about 8 mm; secondary, about 2 mm. Internode length: About 1 to 2.5 cm. Texture: Sparsely pubescent; woody at base. Color: 137A.

*Foliage description*.—Leaves alternate, single. Quantity of leaves per secondary branch: Numerous, about 26. Length, fully expanded leaves, basal: About 5 cm. Width, fully expanded leaves, basal: About 1.5 to 2 cm. Shape: Elliptic to lanceolate. Apex: Broadly acute. Base: Attenuate. Margin: Nearly entire with three to five widely-spaced irregular teeth. Teeth typically present on older leaves. Aspect: Mosty flat. Texture: Smooth; thick and leathery; slightly pubescent on lower surface. Color: Young foliage, upper surface: 137A. Young foliage, lower surface: 137C. Fully expanded foliage, upper surface: 137A. Fully expanded foliage, lower surface: 137C. Attenuated leaf base: 139C. Venation, upper and lower surfaces: 139C.

Inflorescence description:

*Appearance*.—Daisy-type composite inflorescence form; actinomorphic. Single inflorescences displayed above foliage, upright on long peduncles arising from leaf axils. Disc and ray florets arranged acropetally on a capitulum. Typically about 116 opened and unopened inflorescences per plant. Inflorescences last about one week. Inflorescences persistent.

*Flowering response*.—Plants flower continuously from April to October in the Northern Hemisphere.

*Fragrance*.—None detected.

*Inflorescence size*.—Diameter: About 5.5 cm. Depth (height): About 1.5 cm. Diameter of disc: About 1.2 cm.

*Inflorescence buds*.—Length: About 1.6 cm. Width: About 8 mm. Shape: Ovoid. Color: 90B.

*Ray florets*.—Length: About 2.8 cm. Width: About 5 mm. Shape: Spoon. Apex: Tri-dentate, minute. Base: Acute. Margin: Entire. Aspect: Mostly flat to upright. Texture: Smooth, satiny. Number of ray florets per inflorescence: About 16 to 18 in one whorl. Color: When opening, upper surface: 75A to 75B. When opening, lower surface: 79A. Fully opened, upper surface: Apex, 78B; base, 78C; fading to 75C with subsequent development. Fully opened, lower surface: 90C to 90D; fold, 79A.

*Disc florets*.—Shape: Tubular; slightly salverform; five-lobed, fluted at apex. Number of disc florets per inflorescence: Numerous, about 68. Length: About 5 mm. Width: About 1.5 mm. Color: Immature: Apex, 96C; midsection, 85A. Mature: Apex, 96C; midsection, 85D.

*Phyllaries*.—Shape: Linear. Apex: Narrowly acute. Margin: Entire. Quantity and arrangement: About 13 per inflorescence; whorled. Texture: Hirsute. Color: Upper surface: 138C. Lower surface: 138A to 138B.

*Peduncle*.—Length: About 7 cm. Aspect: Moderately strong; inflorescences held above foliage. Texture: Hispid; coarse. Color: 137A.

*Reproductive organs*.—Androecium: Present on disc florets only. Stamens: Five. Anther shape: Oblong. Anther size: About 1 mm. Anther color: 86A. Pollen amount: Moderate. Pollen color: 23A. Gynoecium: Present on ray and disc florets. Pistils: One. Pistil length: About 4 mm. Stigma shape: Bipartate. Stigma color: 86A. Style length: About 3 mm. Style color: 86A. Ovary color: 142D.

*Seed, immature*.—Length: About 5 mm. Diameter: About 2 mm. Color: Green.

Disease resistance: Resistance to pathogens common to Osteospermum has not been observed on plants of the new Osteospermum.

It is claimed:

1. A new and distinct cultivar of Osteospermum plant named 'Pemba', as illustrated and described.

* * * * *

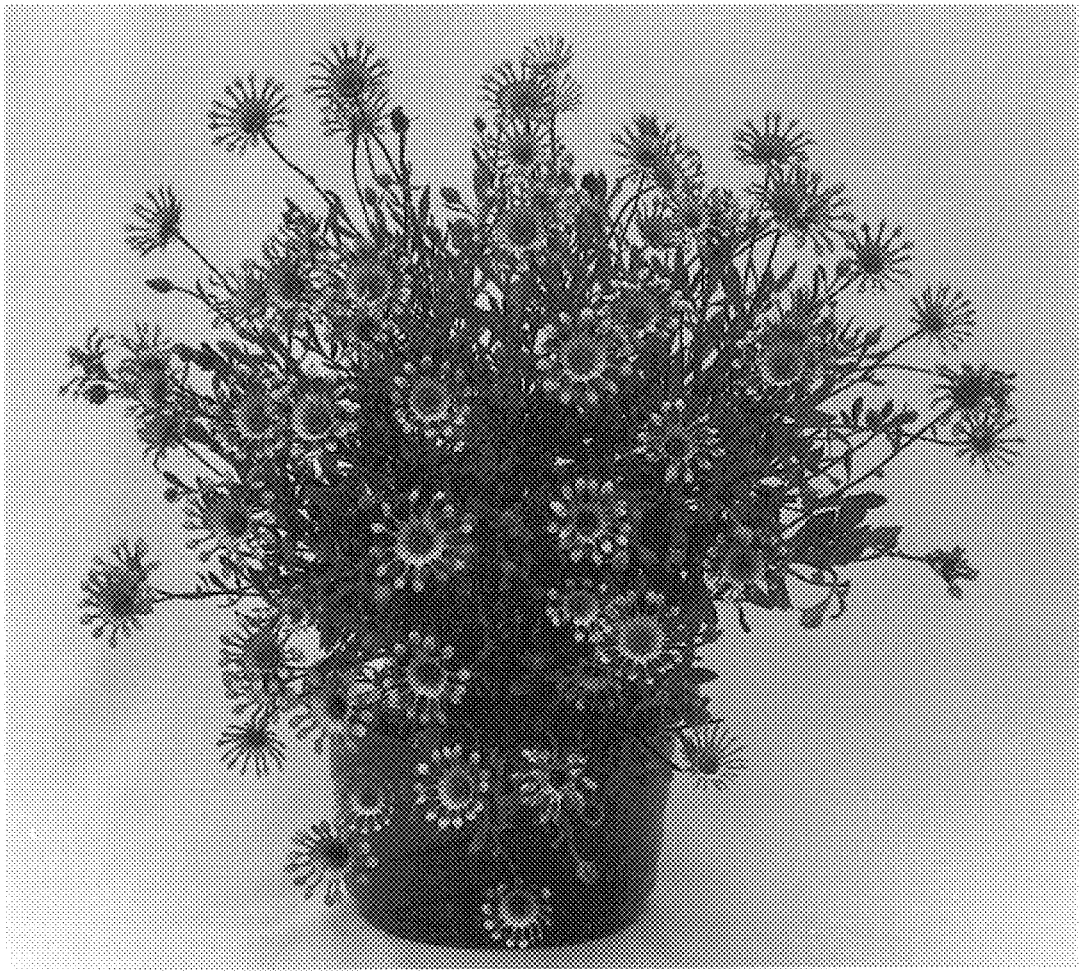
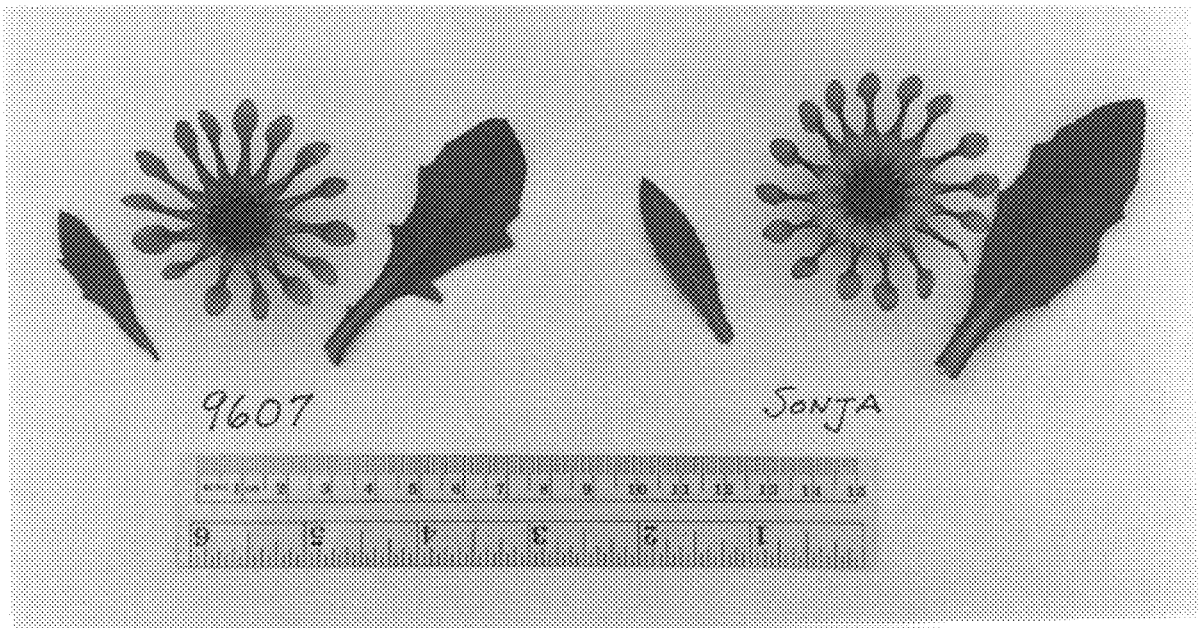
9607
SONJA